United States Patent [19]
Bitdinger et al.

[11] Patent Number: 5,667,495
[45] Date of Patent: Sep. 16, 1997

[54] BACKSTOP DEVICE FOR A SYRINGE

[75] Inventors: Ralf V. Bitdinger, Herbeys; Jean Pierre Grimard, Vif, both of France

[73] Assignee: Becton Dickinson France S.A., Le Ponte de Claix, France

[21] Appl. No.: 426,519

[22] Filed: Apr. 21, 1995

[51] Int. Cl.⁶ ..................................... A61M 5/00
[52] U.S. Cl. .................................... 604/220
[58] Field of Search .................. 604/220, 232, 604/187, 218, 195, 227

[56] References Cited

U.S. PATENT DOCUMENTS

| 3,076,455 | 2/1963 | McConnaughey et al. | 604/232 |
| 4,643,724 | 2/1987 | Jobe | 604/232 |
| 4,711,637 | 12/1987 | Leigh et al. | 604/220 |
| 4,883,471 | 11/1989 | Braginetz et al. | 604/195 |
| 4,946,441 | 8/1990 | Laderoute | 604/110 |

FOREIGN PATENT DOCUMENTS

| 0 242 956 A1 | 10/1987 | European Pat. Off. |
| 0 409 134 A1 | 1/1991 | European Pat. Off. |
| 29 45 869 A2 | 11/1979 | Germany |
| WO 94/26334 | 11/1994 | WIPO |
| WO95/35128 | 12/1995 | WIPO |

*Primary Examiner*—John D. Yasko
*Attorney, Agent, or Firm*—Vincent A. Castiglione

[57] ABSTRACT

A backstop device to prevent inadvertent withdrawal of a stopper from the open distal end of a syringe barrel. The backstop, mounted to a syringe flange, includes a pair of spaced apart plates located on either side of the flange. Both plates include respective apertures accessible through lead openings formed through the plates. The bottom aperture is formed for snug contact with the syringe barrel, while the upper aperture includes a ridge engageable with the interior of the syringe barrel adjacent the open distal end. The top aperture and ridge together present a smaller passageway than the diameter of the stopper, preventing inadvertent removal thereof. The backstop can be placed on the syringe regardless of the presence or absence of the plunger.

20 Claims, 18 Drawing Sheets

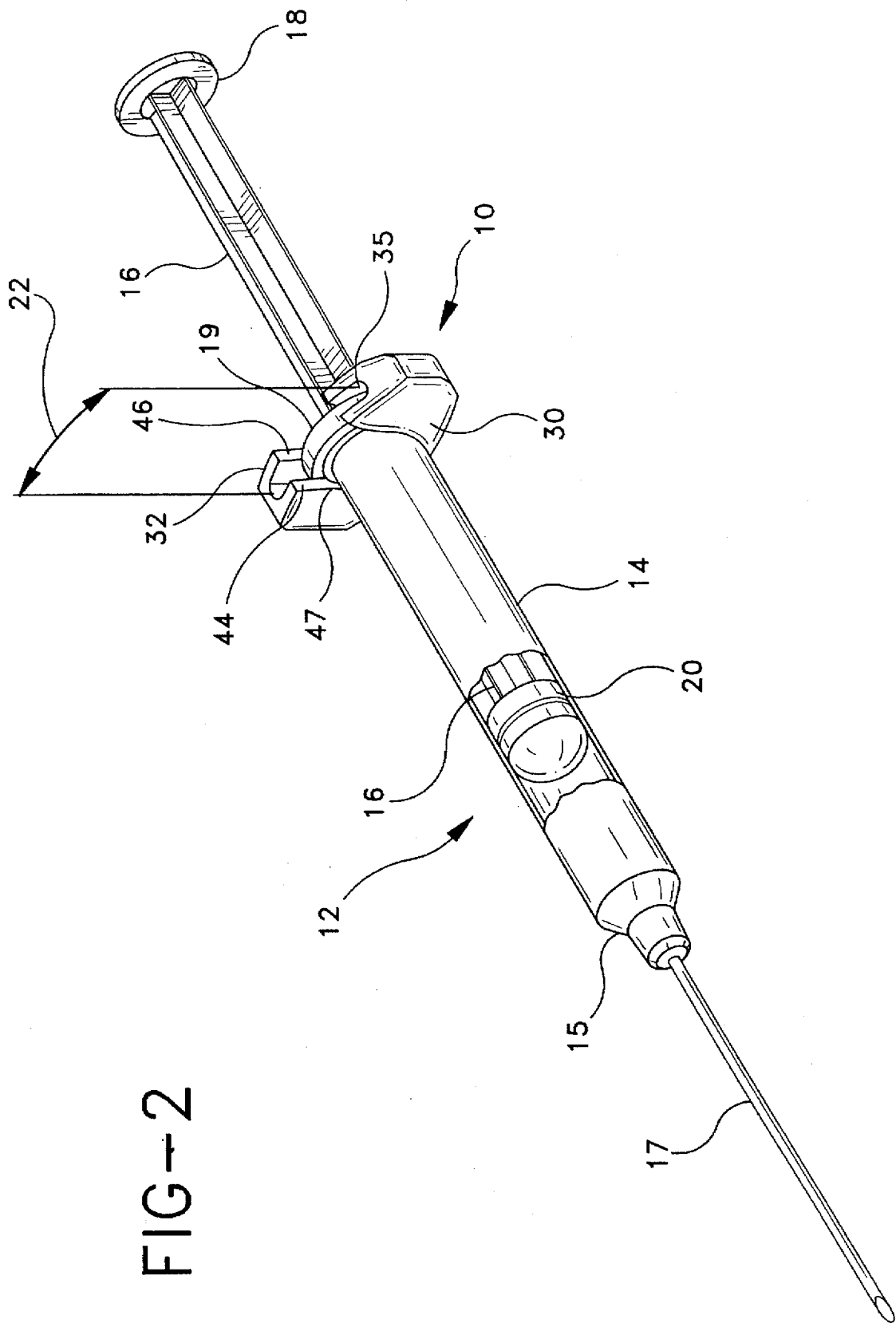

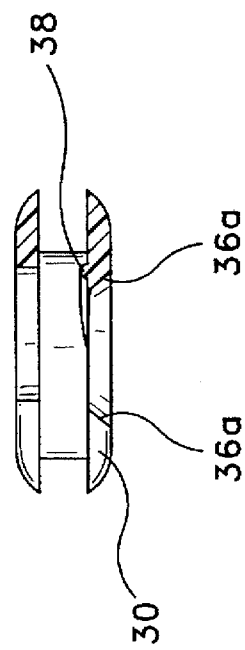
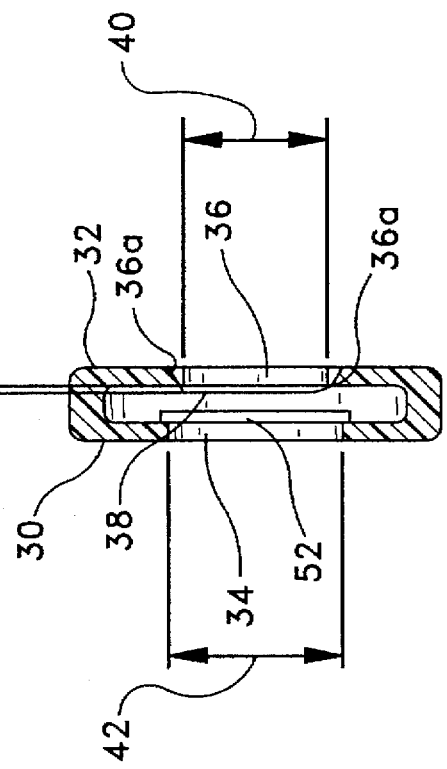

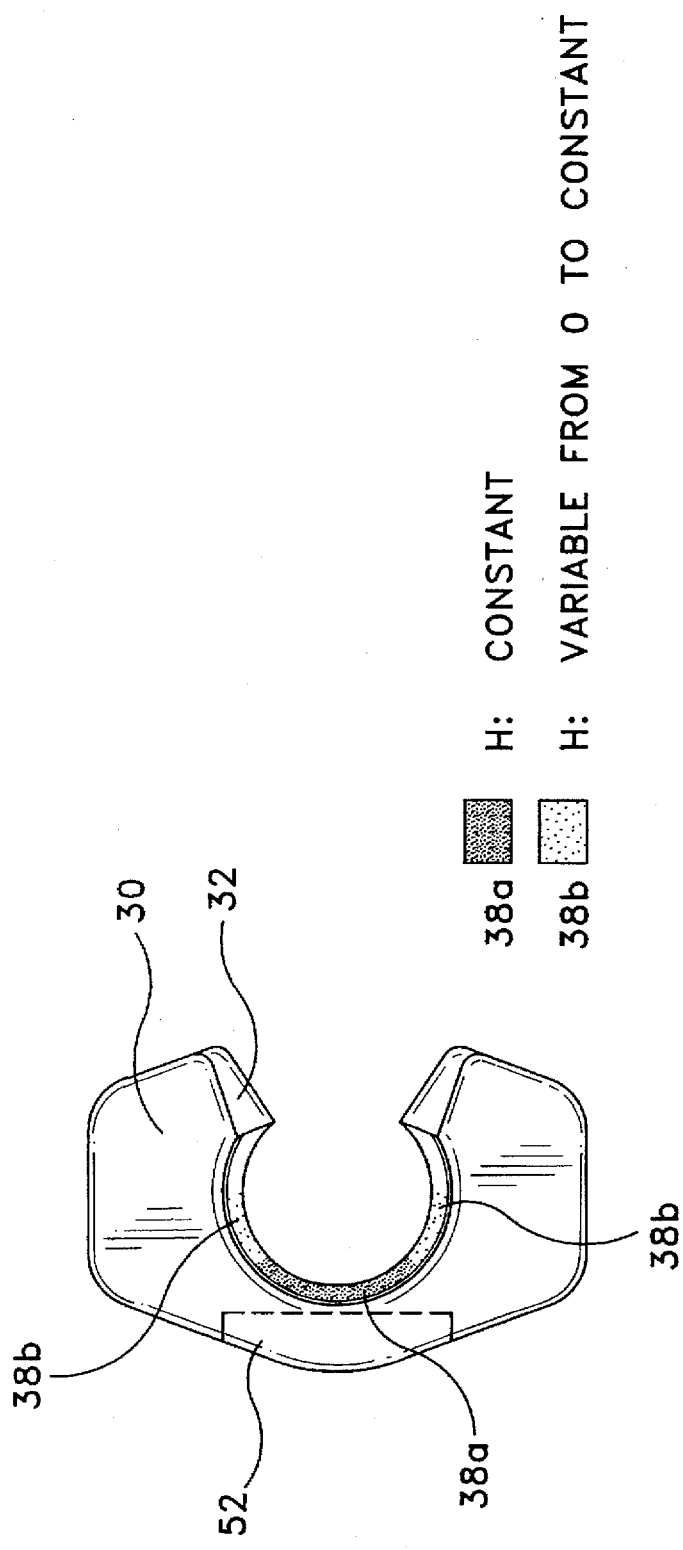

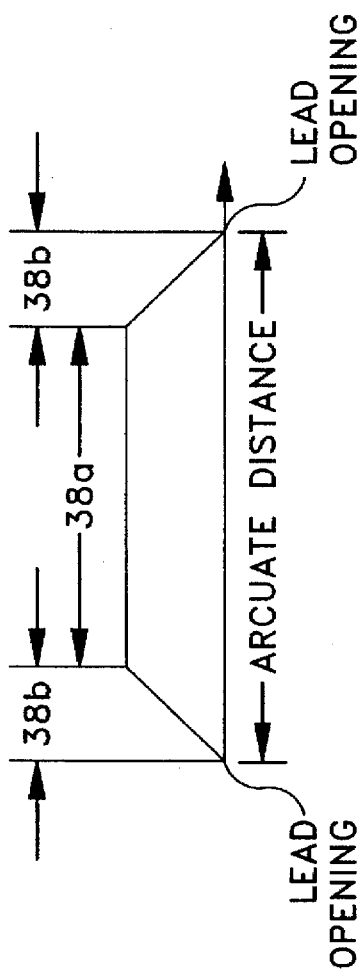
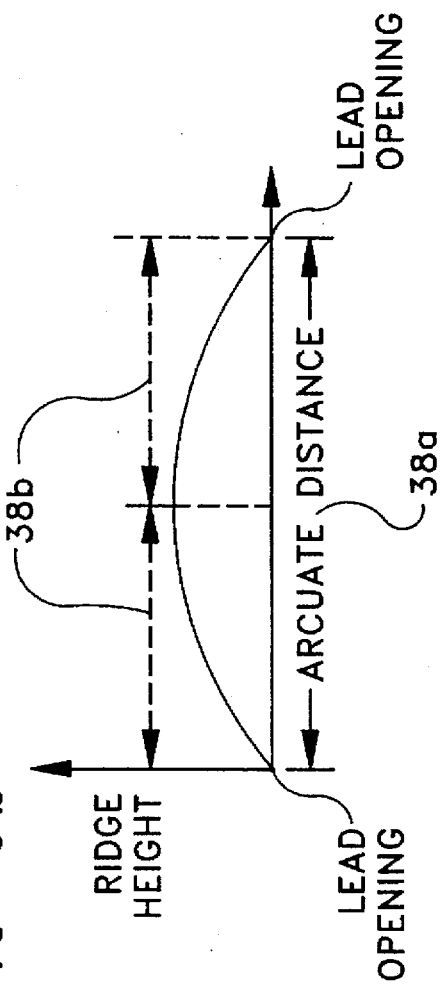

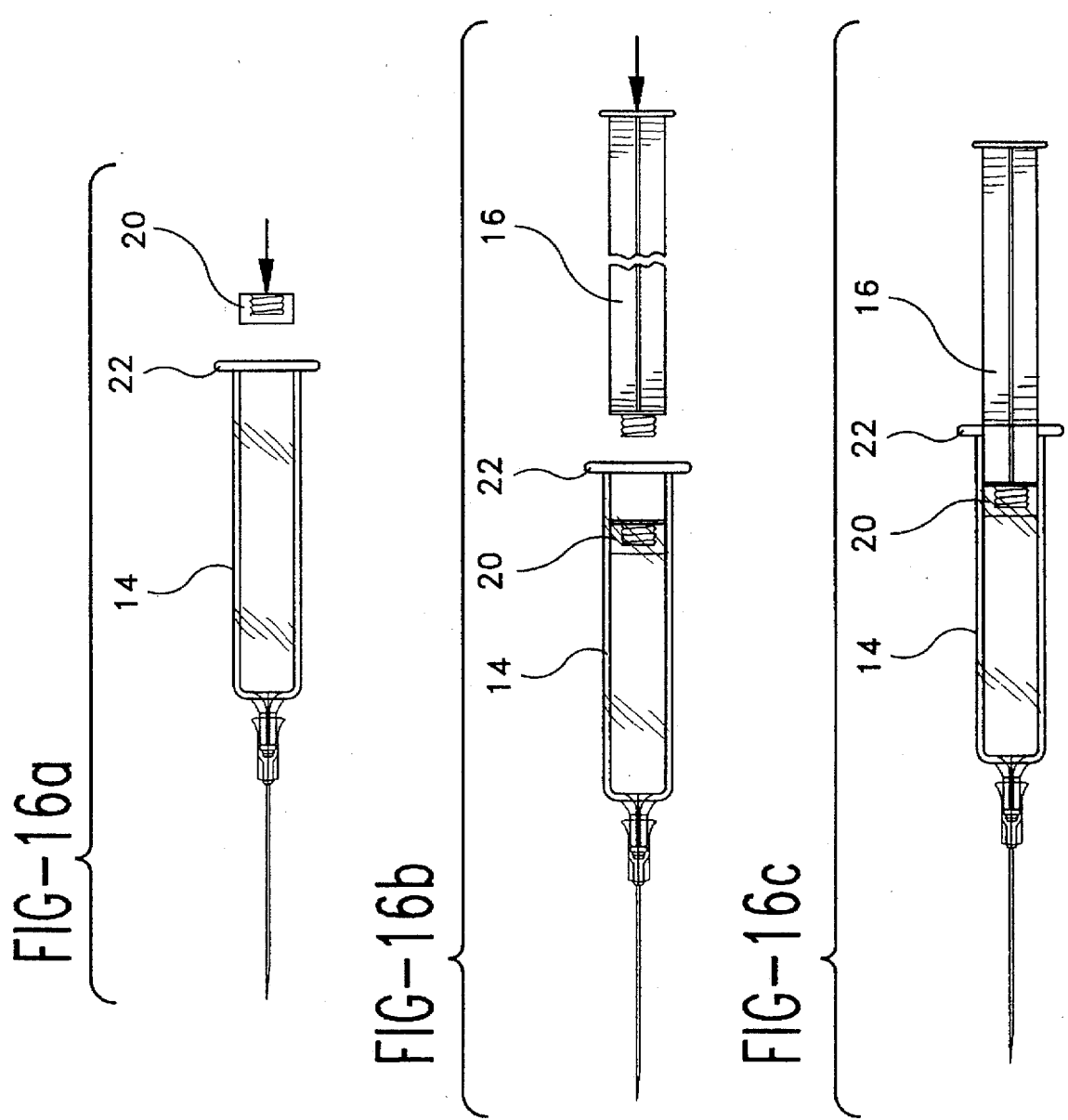

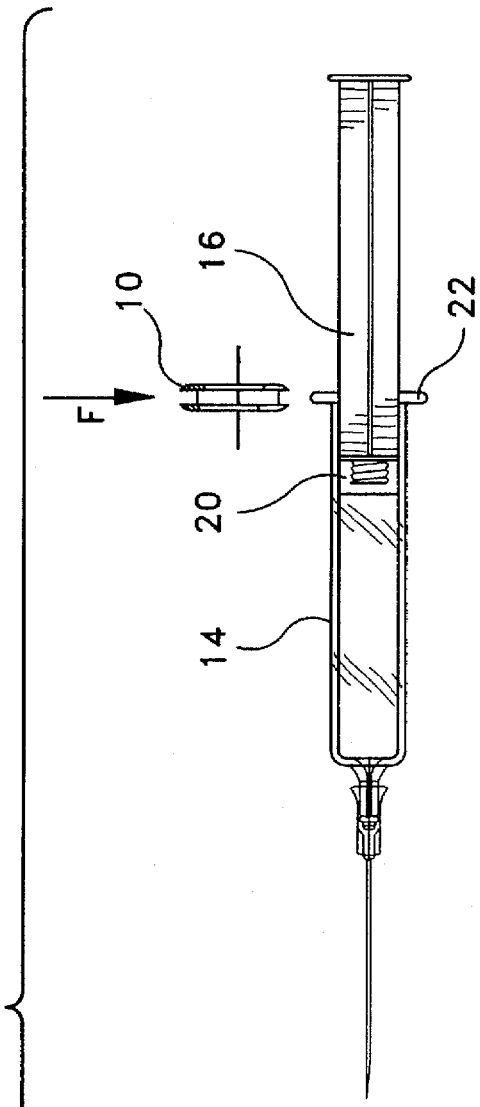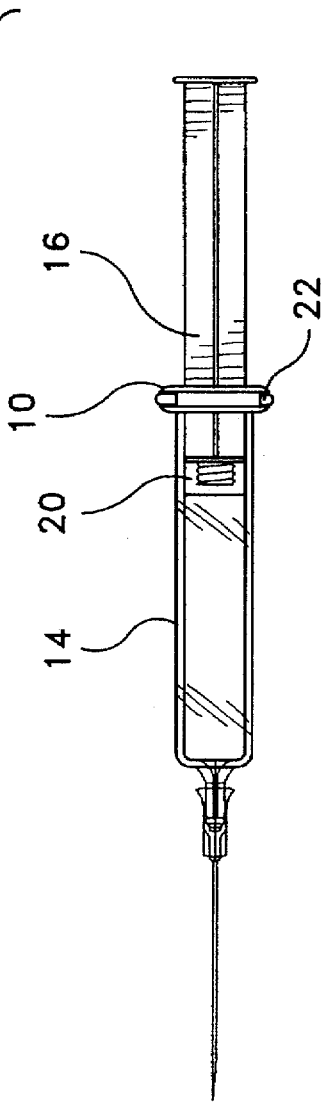

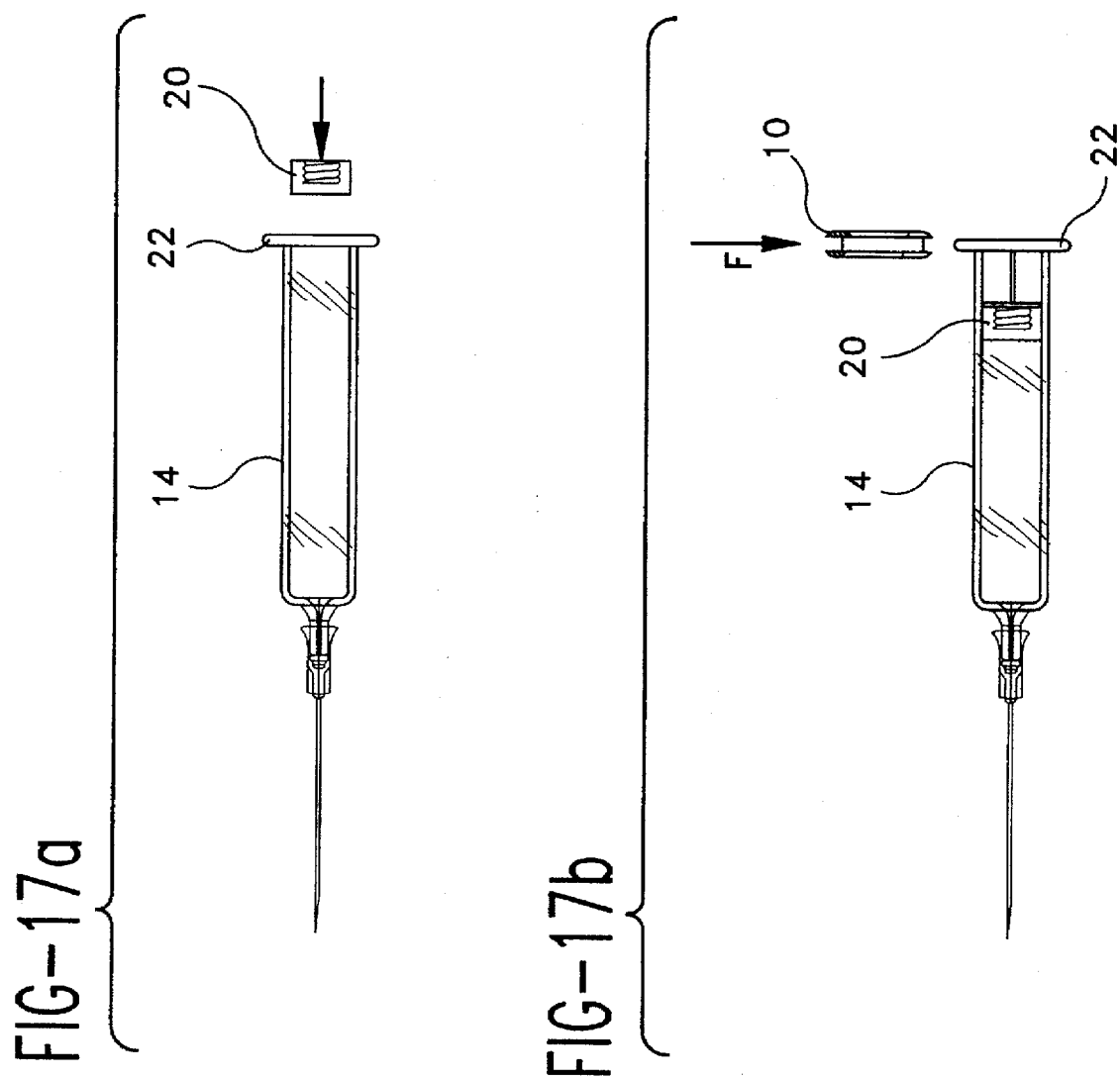

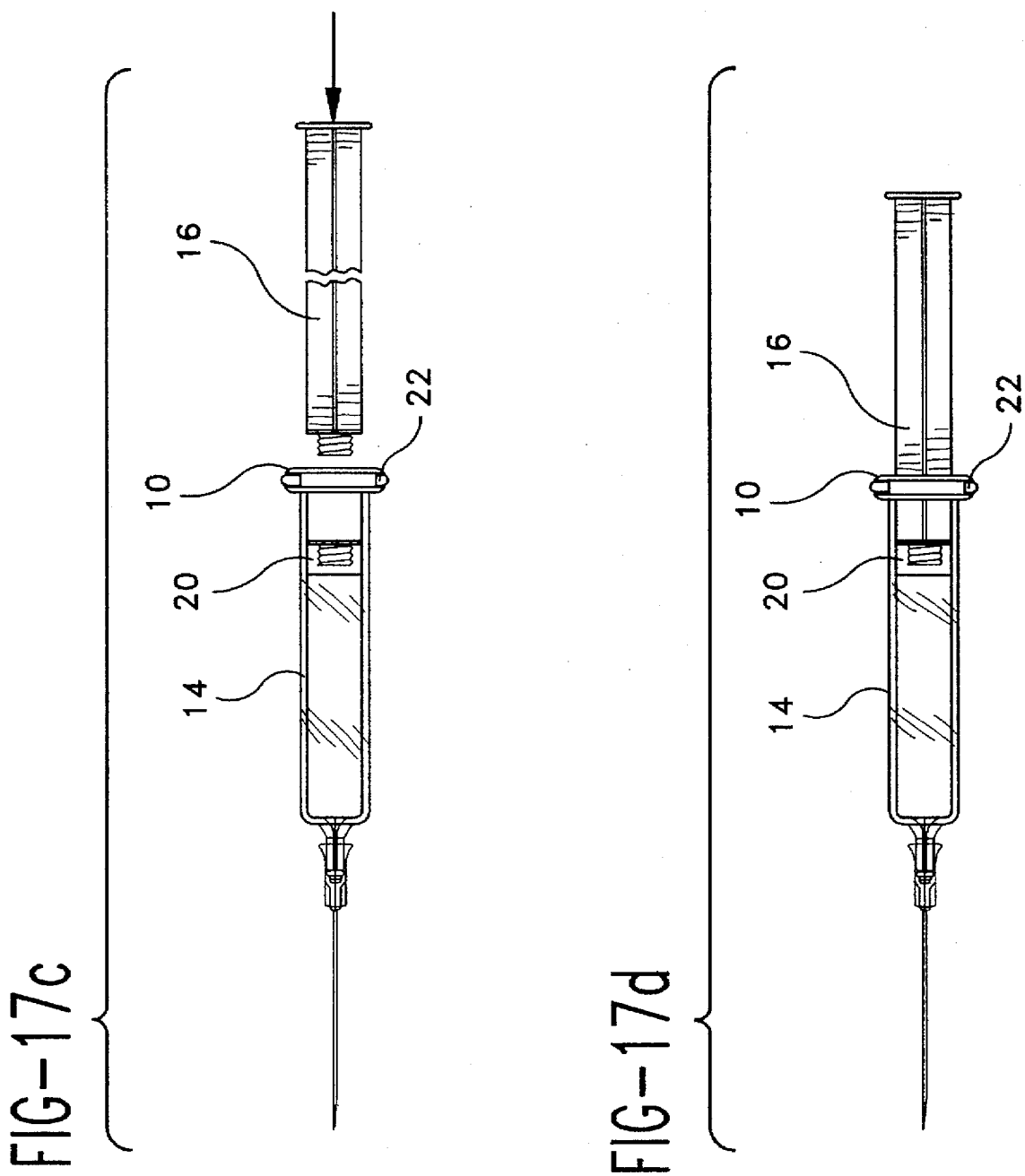

BACKSTOP DEVICE FOR A SYRINGE

FIELD OF THE INVENTION

The invention relates to a backstop device for a syringe, and more particularly, to a backstop device for a syringe which prevents inadvertent removal of the stopper component associated with the syringe.

BACKGROUND

As is known in the art, syringes are medical delivery devices utilizable to administer a medicament to a patient. Syringes are normally marketed either in prefilled form, wherein a set dosage of medicament is already provided therein, or they are empty and intended to be filled from a vial or other source of medicament by an end user at the time administration of the medicament is desired.

Syringes typically include a barrel portion adapted to retain the medicament. The distal end of the barrel is normally configured to mate with a conventional piercing element, such as a pointed needle cannula made of steel or like material or a blunt ended cannula formed of plastic, to deliver the medicament contained in the barrel. A plunger rod is inserted through the open distal end of the syringe barrel and, through its engagement with an elastomeric or rubber-like stopper element fitted in a fluid-tight manner within the interior of the barrel, a user can apply manual force to the plunger to deliver the medicament through the piercing element. A flange is also typically provided around the open distal end of the syringe barrel as a form of finger rest to facilitate a user's manipulation of the device.

As the skilled artisan will appreciate, one problem with either pre-filled syringes or empty syringes is that the stopper element can be inadvertently dislodged from the syringe barrel, rendering the syringe itself unusable and/or the medicament therein unsterile. For instance, particularly in the case of prefilled syringes, forces exerted on the stopper during terminal sterilization procedures could cause the stopper to eject from the open distal end of the syringe, rendering the product unusable. Also, end users attempting to aspirate medicament through the piercing element into the syringe barrel could, inadvertently, exert excess force onto the plunger, causing the stopper to dislodge from the barrel. There is also the risk that for certain medicaments, such as cytotoxic drugs, that safety concerns dictate that the stopper not be dislodged from the barrel.

Numerous attempts in the art have sought to address the aforementioned concerns. For instance, U.S. Pat. No. 4,711,637 to Leigh et at. describes a syringe lock formed as a clip made from a malleable material such as sheet metal. The clip, affixed to the proximal end of the syringe, includes a protrusion jutting towards the interior portion of the barrel which serves to "bite" into the plunger so as to arrest movement thereof once a desired plunger position is achieved. In this type of device, inadvertent rotation of the plunger could cause unwanted locking, rendering the syringe unusable. Another clip-type approach is found in U.S. Pat. No. 4,883,471 to Braginetz et al., wherein a spring clip is disposed around the exterior of the syringe barrel. The clip includes finger elements protruding through apertures formed in the syringe barrel. The finger elements physically arrest the stopper element once a desired plunger extension is reached.

Alternately, structure may be incorporated as part of the syringe barrel itself to physically restrain the syringe stopper from inadvertent withdrawal. Examples of these approaches are found, inter alia, in U.S. Pat. No. 4,946,441 to Laderoute and European Patent Application No. 0 409 134 to Escudero. These approaches are oftentimes uneconomical in that costly modifications will be required to molding equipment to achieve the desired structure. In addition, by employing specific, integral syringe barrel construction, the user is deprived of the ability to effect easy, intentional removal of the stopper by disabling the stopper lock structure, if such action is desired.

PCT Application WO 94/26334 discloses, inter alia, two embodiments of a plunger lock device for a syringe. A first embodiment is of the spring clip type and includes a finger portion 61 jutting into the interior of the syringe barrel. The finger portion 61 physically arrests the stopper from inadvertent withdrawal. A second embodiment entails a disk-like addition which mounts to the flange area of the syringe. The top portion of the disk includes an aperture, aligned with the syringe barrel, that is smaller than the internal diameter of the barrel. While the smaller diameter disk aperture prevents the stopper from inadvertent withdrawal, this embodiment can only be effected where the disk is first mounted to the syringe flange and the plunger thereafter inserted through the disk aperture for attachment to the stopper. Accordingly, the disk device as taught therein is mainly intended for use where it is shipped intact with a fully assembled syringe, and most likely where affixation of the plunger lock device is part of the syringe filling, assembly and/or sterilization processes. Most syringe processing machinery, however, is not set up to accommodate manipulation of the lock device, and modifications to the production line can be costly if not difficult. For reasons of economy, and particularly where specialized filling or sterilization machinery is already in place, it would be advantageous to ship the device apart from a pre-filled or pre-assembled syringe for later affixation. Moreover, it would also be advantageous to permit affixation of the brake device as an add-on component, without having to disrupt the plunger from the stopper.

SUMMARY OF THE INVENTION

These and related concerns are addressed by a syringe backstop device in accordance with the present invention. The device, readily applicable to either plastic or glass syringes, is preferably formed as a plate-like structure, and may be adapted to the dimensions of the syringe flange in a manner to enhance a user's grip of the device. In one embodiment, the backstop includes spaced apart top and bottom plates allowing the device to be fitted to the flange. Each plate includes respective apertures therethrough, the bottom aperture preferably conforming to the exterior dimensions of the syringe barrel, while the top aperture includes a ridge element adapted to snugly fit with the interior diameter of the syringe barrel. In one configuration, the top aperture is formed through the top plate in a frusto-conical configuration, with the ridge element disposed at the bottom of a lead wall defined by the frusto-conically shaped top aperture. The ridge acts both to enhance retention of the device with the syringe and to serve as a physical barrier preventing the stopper from inadvertent withdrawal from the syringe barrel. Each of the plate apertures includes a lead opening through its respective plate to permit the mounting of the device to the syringe flange, regardless of the presence or absence of the plunger. The openings are further dimensioned to accommodate flanges of varying shapes irrespective of the angular orientation of the openings with respect to the flange. The lead openings include transition edges extending from the lead opening to the respective aperture. The bottom lead opening may be formed to guide the user in placing the device onto the syringe. The bottom transition edges may be formed with a wider rake respective of top transition edges for the same purpose. A rib element, preferably located adjacent either of the top or bottom plates, or both, and preferably opposite the lead openings, may be configured for engagement with a portion of the flange so as to minimize inadvertent rotation or play of the device.

BRIEF DESCRIPTION OF THE DRAWINGS

The invention will now be described in greater detail by way of reference to the appended drawings, wherein:

FIG. 2 depicts the backstop device of the present invention mounted to a conventional syringe;

FIG. 7 is a side cut-away view of the embodiment of the backstop illustrated in FIG. 1;

FIG. 8 is a partial cut-away, frontal view of the backstop illustrated in FIG. 1;

FIG. 9 is a second bottom view of the embodiment illustrated in FIG. 1, depicting one formation of the ridge;

FIG. 9a is a graphical illustration of the progression of the height of the ridge as seen in FIG. 9;

FIG. 9b is a graphical illustration of an alternate progression of the height of the ridge;

FIGS. 16a–16e illustrate placement of the backstop relative to the flange after the plunger is assembled onto the syringe;

FIG. 17 (17a to 17d) depicts placement of the backstop relative to the flange before assembly of the plunger onto the syringe;

DETAILED DESCRIPTION OF THE INVENTION

Figure 12B:
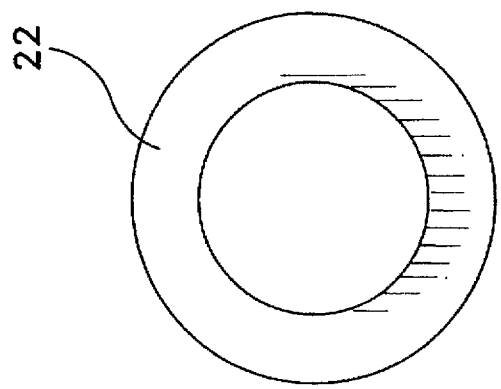
FIG. 12 (12a and 12b) depicts two possible shapes of flanges utilized on syringes.

Turning now to the drawings, wherein like numerals denote like components, FIGS. 1 and 3–15 depict one embodiment of a backstop 10 in accordance with the present invention. FIG. 2 illustrates the backstop 10 in perspective as mounted to a medical delivery device such as a syringe 12. As depicted, syringe 12 generally includes a syringe barrel 14 adapted to contain a medicament therein, with the barrel 14 featuring a distal end 15 adapted in a conventional manner for attachment or mating with the piercing element 17 as previously described. For instance, distal end 15 could be formed as a male luer connector. A relatively open proximal end 19 is formed at the opposing end of the syringe barrel, through which a plunger 16 is inserted. The plunger 16 mates with a stopper element 20 disposed in fluid-tight engagement with the interior of syringe barrel 14. The plunger 16, which generally is provided separate from the stopper 20, may mate with stopper 16 via a screw-type or other arrangement, as the skilled artisan will appreciate. The plunger 16 typically includes a finger rest 18 provided at its proximal end for manipulation by a user; likewise, syringe 12 typically also includes a flange 22 adjacent the open proximal end 19, forming a type of finger rest permitting the user to manipulate the syringe 12 during use. As depicted in FIG. 12, the flange 22 may take various shapes such as round (FIG. 12b) or, as oftentimes seen, a type of modified rounded, which includes a pair of straight sides 50 (FIG. 12b), as the skilled artisan will appreciate.

As depicted herein, backstop 10 in accordance with the present invention is configured for mating with a syringe 12 via the flange element 22. It will be appreciated and understood by those skilled in the art, however, that the backstop 10 in accordance with the invention may be applied to other medical delivery devices, where it is desired to avert inadvertent withdrawal of an element such as stopper 20.

Figure 20:
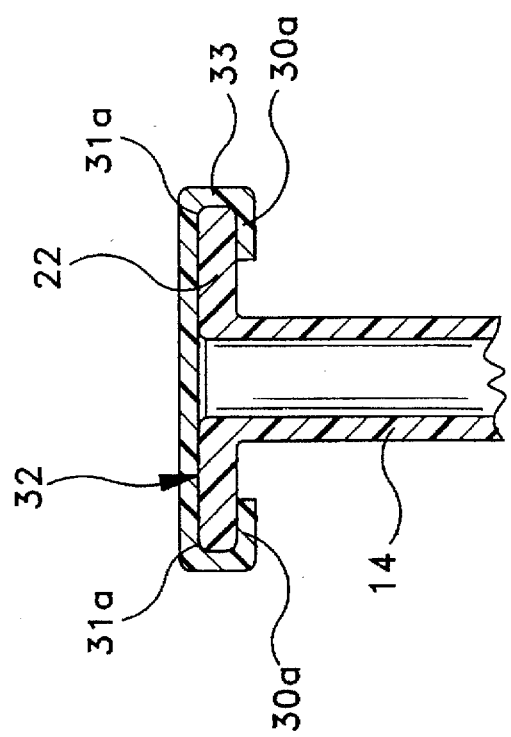
FIG. 20 is a cross-sectional view illustrating the embodiment of FIG. 19 mounted to a syringe.
Figure 19:
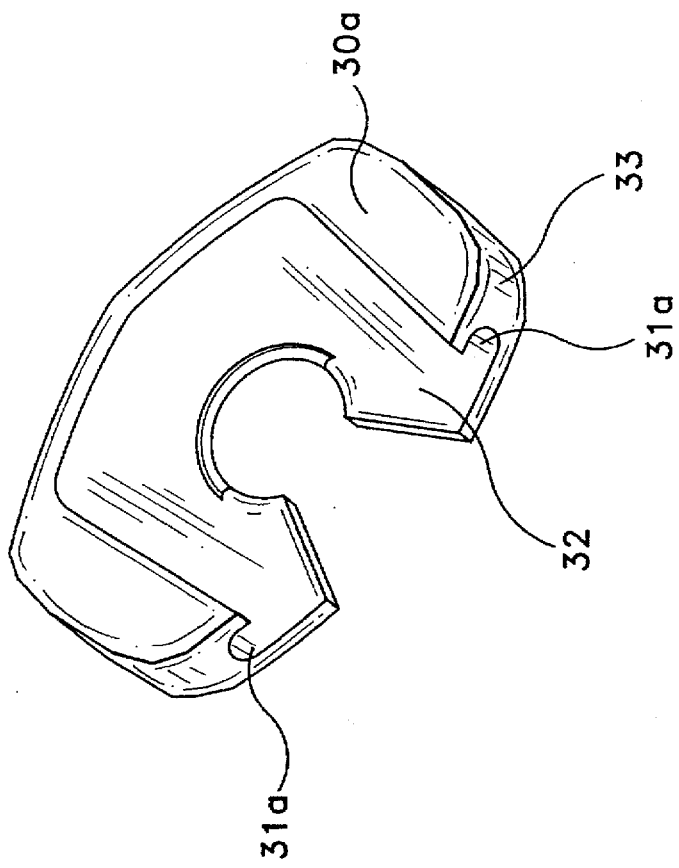
FIG. 19 is a bottom view of an alternative embodiment of the backstop device of the invention.

Turning now more particularly to FIGS. 1 through 15, one embodiment of backstop 10 in accordance with the invention features a bottom plate 30 and a top plate 32, spaced apart from one another so as to create therebetween a pocket-type enclosure 31 which is dimensioned and configured to accommodate therein flange 22 of the syringe. As will be explained hereinafter, if desired, bottom plate 30 may be eliminated in favor of a top plate extension portion 30a (see FIGS. 19 and 20) which locks about flange 22.

The enclosure 31 includes a frontal opening 35 through which flange 32 enters enclosure 31. As depicted and more fully explained with reference to FIG. 18, frontal opening 35 is configured and dimensioned in a manner to permit the mounting of backstop 10 over flange 22 regardless of the angle of approach or orientation between flange 22 and backstop 10. Side walls 33 may serve to connect top and bottom plates 32 and 30, respectively, and help define enclosure 31. It will be appreciated and understood by those skilled in the art that backstop 10 may be formed in any one of conventional manners such as injection molding. It may be formed from appropriate medical grade plastics, hard rubber materials, glass, metals or the like.

While the top and bottom plates 32 and 30 are herein depicted as relatively flat, if desired, either one or both of them can be formed with a concave shape (see FIG. 11) such that the plates are free to flex towards and away from enclosure 31. In this manner, either or both of the top and bottom plates 32, 30 may flex as the backstop 10 is placed about flange 22, thereby accounting for any tolerance deviations, inconsistencies of shape or surface, or other difficulties displayed by the flange 22. Also, in this manner, backstop 10 may exert a more positive holding action onto flange 22, should such increased force be necessary or desirable. While not depicted in the Figures, the skilled artisan will also appreciate that the device in general may be dimensioned and configured so that the plates may assume a convex shape to achieve the same purpose.

An aperture is provided in each of top and bottom plates 32 and 30. Bottom plate aperture 34 is generally configured and dimensioned for form fitting contact with the exterior surface of syringe barrel 14, while top plate aperture 36 is generally dimensioned to accommodate insertion of syringe plunger 16 therethrough. As will be explained in greater detail hereinbelow, the aperture 36 itself and/or the structure associated therewith forms a passageway through plate 32 that is somewhat smaller than the internal diameter defined by open distal end 19 of syringe barrel 14. As herein shown, bottom aperture 34 is formed in a relatively arcuate manner so as to conform to the relatively cylindrical outside surface of syringe barrel 14. However, the shape of the aperture is not necessarily so limited and, as can be appreciated, can be configured to accommodate any shape taken by syringe barrel 14, such as ovoid, square, etc.

Both to permit insertion of backstop 10 about the flange 22 and to permit the insertion of the backstop regardless of the presence or absence of plunger 16, each of the respective plate apertures 34, 36 may be provided with lead openings formed or otherwise cut through the plates. Thus, bottom plate 30 features a lead opening 42, which is connected to aperture 34 via a pair of transition edges 44. Transition points 45 define the parameters demarcating bottom aperture 34 from transition edges 44. Likewise, top plate opening 40 is connected to top plate aperture 36 via a pair of top plate transition edges 46, whose demarcation from top aperture 36 is noted by transition points 47. As will be seen the figures, both of the lead openings 40, 42 are themselves encompassed by frontal opening 35 of the device.

As best seen in FIGS. 3 through 6, where syringe barrel 14 is relatively cylindrical, bottom aperture 34 can be formed, for instance, in an arcuate manner extending at least equal to if not greater than 180°, such that the chordal distance between transition points 45 is formed least equal to, if not slightly less than, the outside diameter of syringe barrel 14. In this manner, when backstop 10 is fitted to the syringe, the syringe barrel 14 may be urged past the transition points 45. The aperture 34 can expand slightly to accommodate the syringe barrel 14, such that when the backstop 10 is in place respective of flange 22, transition edges 45 will re-contract about the syringe barrel 14, causing aperture 34 to exert a positive holding action therewith. As also will be seen in the Figures, the width of bottom opening 42 can be configured slightly greater than the width of top opening 40, in a manner that the bottom opening 42 may readily guide the user 42 into easily placing backstop 10 around the syringe barrel 14 for placement about flange 22.

Figure 1:
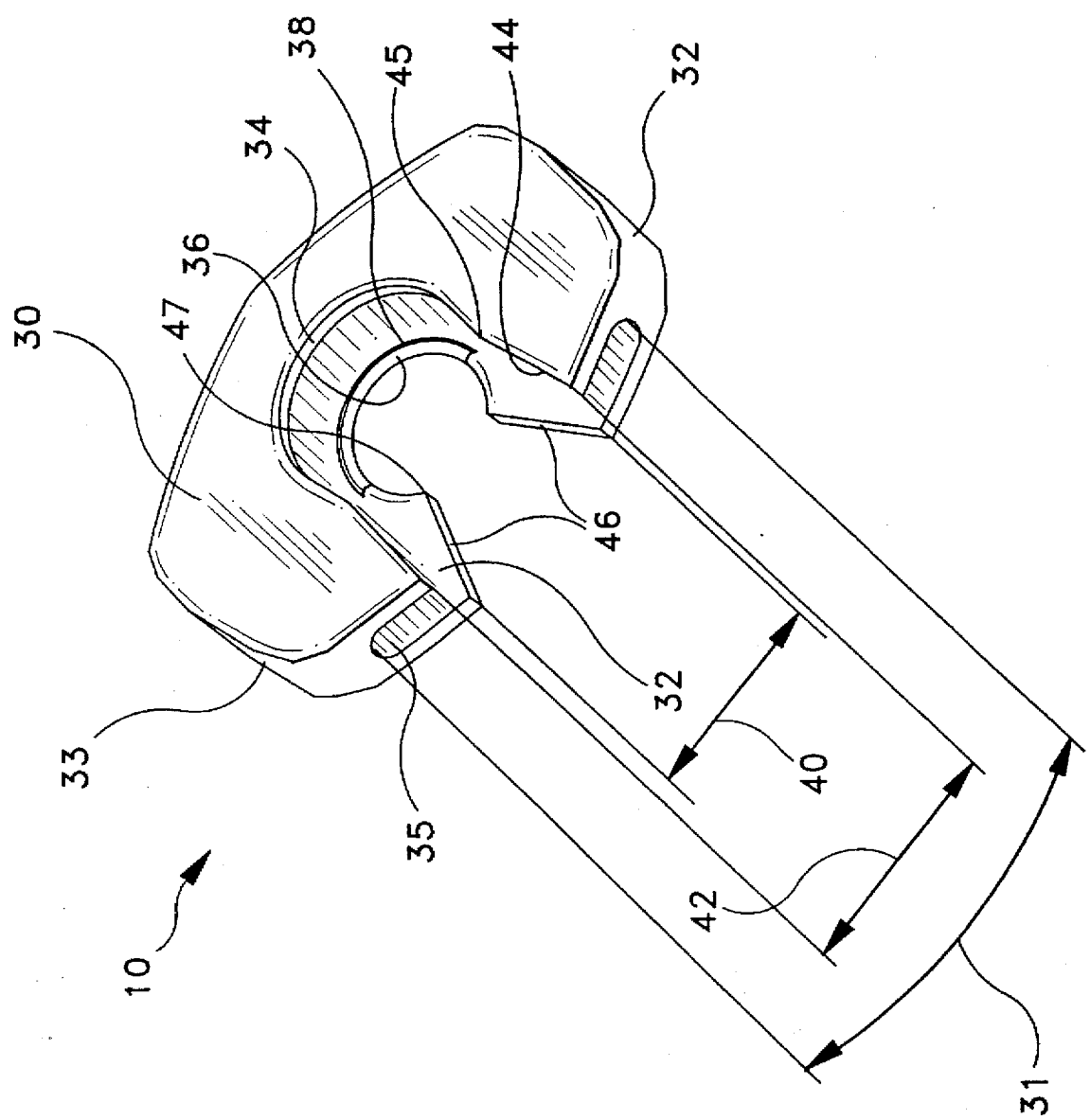
FIG. 1 depicts, in bottom perspective view, one embodiment of a backstop device in accordance with the present invention.
Figure 4:
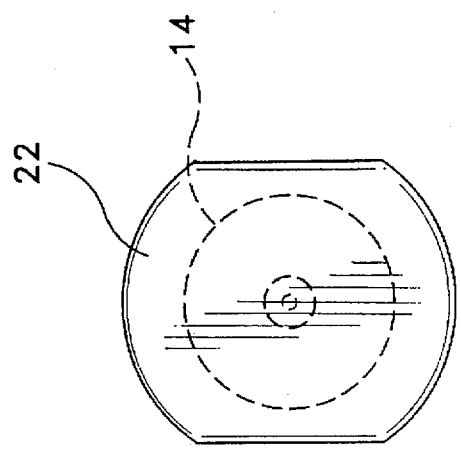
FIG. 4 is a top view illustrating a conventional syringe flange.
Figure 3:
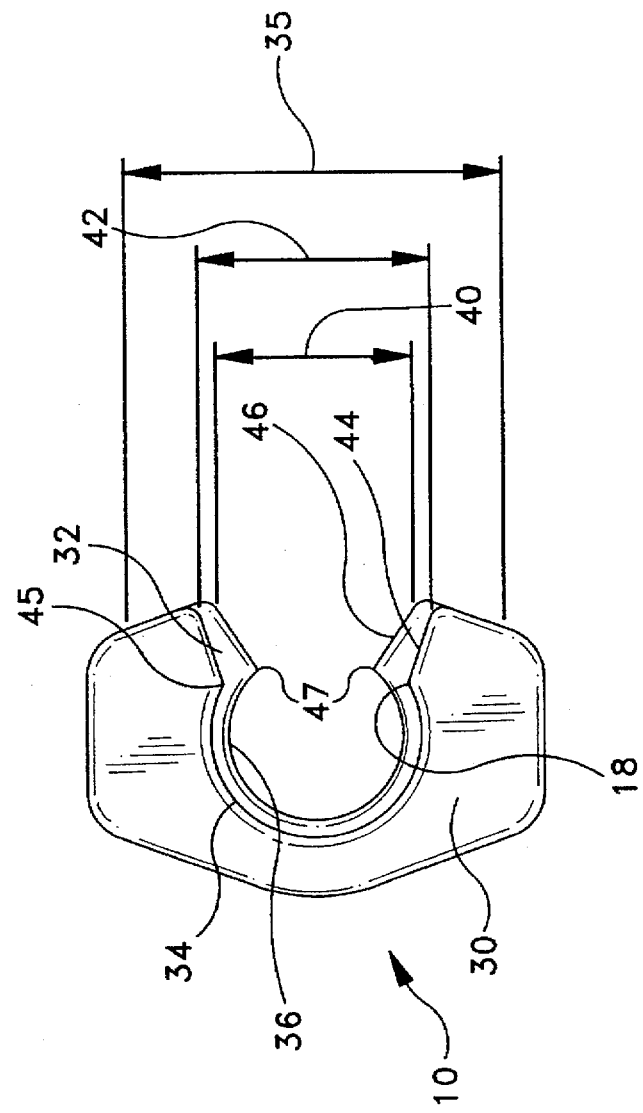
FIG. 3 is a bottom view of the embodiment depicted in FIG. 1.
Figure 6:
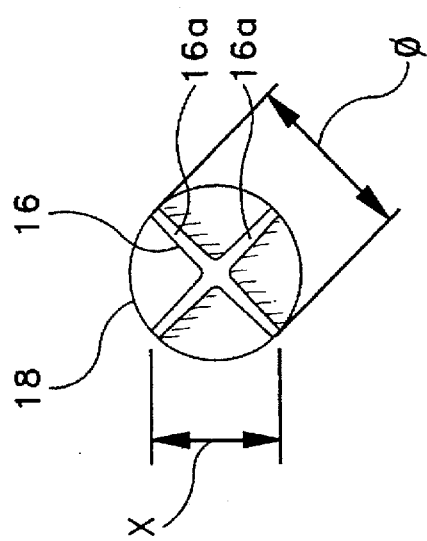
FIG. 6 is a top view illustrating a conventional syringe plunger.
Figure 5:
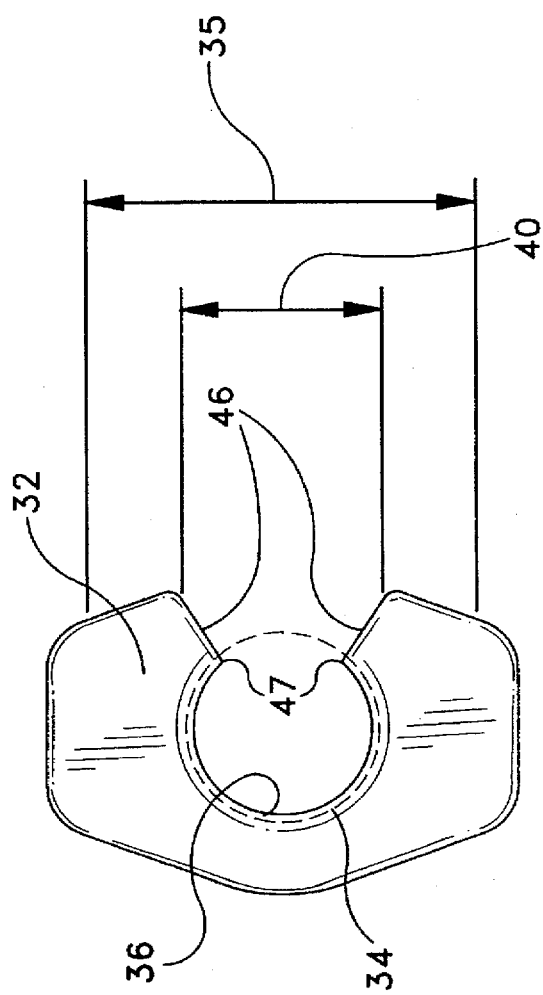
FIG. 5 depicts a top view of the backstop illustrated in FIG. 1.
Figure 11:
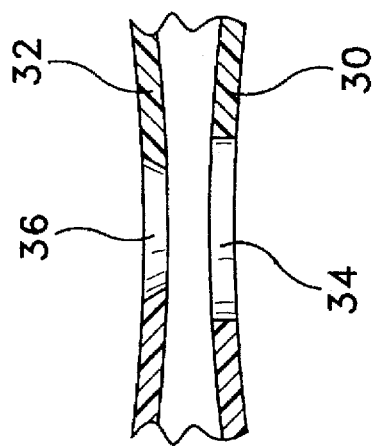
FIG. 11 depicts one embodiment of the backstop device in accordance with the present invention wherein the top and bottom plates are formed with concave surfaces.
Figure 10:
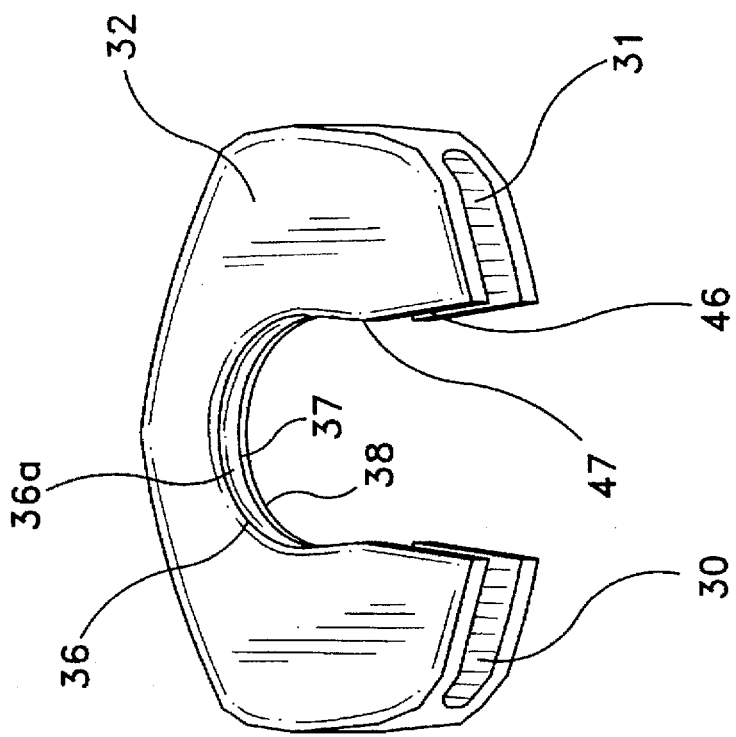
FIG. 10 is a top perspective view of one embodiment of the backstop in accordance with the present invention.

Turning now more particularly to FIGS. 1, 7, 9 and 10, top plate 32 and, in particular, top aperture 36 is structured both to prevent inadvertent withdrawal of stopper 20 from the open distal end 19 of the syringe barrel 14, as well as to enhance secure locking retention of backstop 10 relative to syringe barrel 14. It also permits plunger rod 16 to be inserted through aperture 36 when the backstop 10 is already placed on the flange, or allows backstop 10 to be placed on flange 22 when the plunger rod is already in place. As previously noted, the diameter of aperture 36 is formed large enough to permit insertion of plunger rod 16 therethrough. As seen in FIGS. 5 and 6, plunger rod 16 is normally formed from a plurality of vanes 16a, defining a minimum width "X" and a maximum width "ø". The chordal distance between transition points 47 may be formed at least equal to if not slightly greater than "X" to permit rod 16 to access the aperture 36 via the opening 40.

Top aperture 36 is formed through the width of top plate 32 in a manner to define a frusto-conical sloping wall 36a which extends about the periphery of top opening 36. Frusto-conical wall 36a serves to guide insertion of plunger rod 16 and, if need or desire dictate, permits insertion of stopper 20 into syringe barrel 14 through the backstop 10, if already fitted to the syringe.

A ridge element 38 is formed about the periphery 37 of the aperture 36. As herein depicted, the ridge 38 is relatively continuous, but if need or desire dictate, ridge 38 can be formed in discontinuous sections from a plurality of individual ridge elements 38. The ridge element 38 may take any number of configurations, but as depicted in FIG. 13, ridge element 38 extends below periphery 37 in a frusto-conical manner towards the interior of syringe barrel 14. It also further constricts the diameter of aperture 36 as defined around periphery 37. Notably, the diameter measured at periphery 37 should be formed large enough to accommodate insertion of plunger rod 16 therethrough.

Figure 13A:
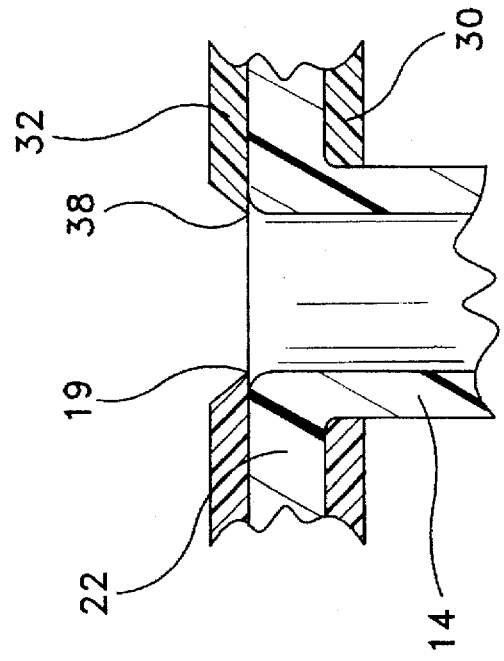
FIG. 13a depicts a second frontal cross-sectional view depicting the backstop mounted to a syringe and flange.
Figure 13:
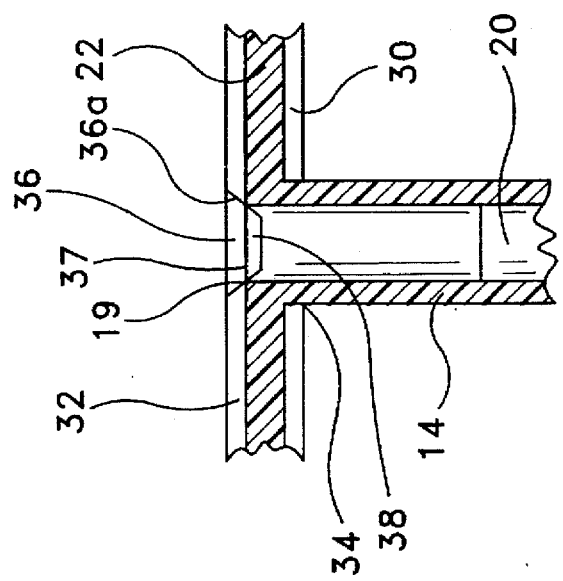
FIG. 13 is a frontal cross-sectional view depicting the backstop mounted to a syringe and flange.
Figure 15:
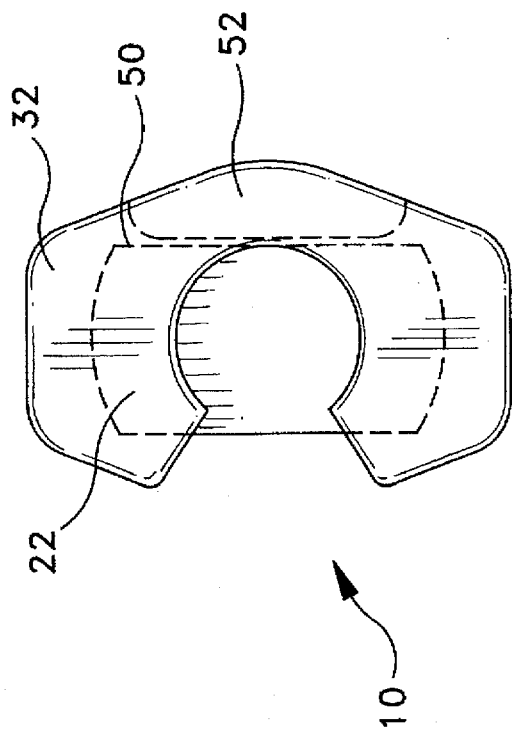
FIG. 15 is a top view of the backstop mounted to the flange of a syringe and illustrating the positioning of the rib relative to the flange.
Figure 14:
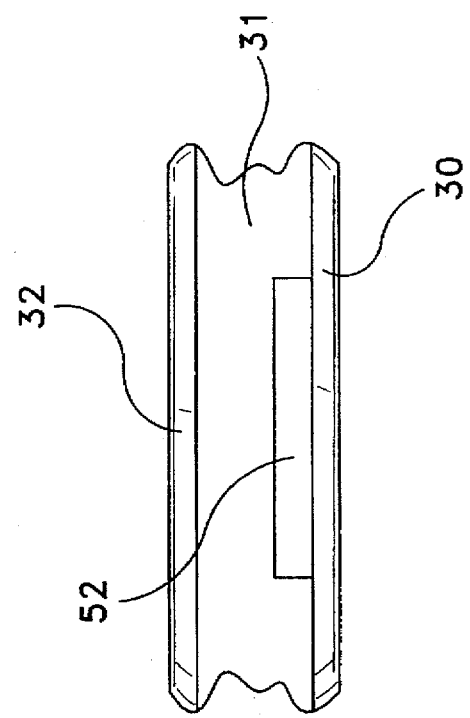
FIG. 14 is a partial rear view of the backstop illustrating placement of the rib relative to the top and bottom plates.

If desired, as depicted in FIG. 13a, ridge element 38 can be configured to contact a portion of syringe barrel 14, either adjacent the intersection between proximal end 19 and the flange 22, or as previously noted respective of FIG. 13, with a portion of interior surface of syringe barrel 14 adjacent the open proximal end 19. Thus, once backstop device 10 is fully fitted about flange 22, sloping wall 36a and the outside periphery of ridge 38 contact the interior surface of syringe barrel 14 (or, as noted above, adjacent the intersection between proximal end 19 and the flange 22) so as to enhance locking retention of backstop 10 to the syringe barrel 14. Moreover, owing to the smaller diameter aperture 36 vis-à-vis the internal diameter of syringe barrel 14, stopper 20 is prevented from inadvertent withdrawal from syringe barrel 14, assisted in this case by engagement with the inwardly facing edge of ridge 38 if withdrawal is attempted. Note that by providing the frusto-conical wall 36a about the periphery of aperture 36, a user may insert stopper 20 into the syringe barrel 14 even if backstop 10 is in place about flange 22, if such action is desired. However, ridge 38 will make contact with stopper 20 to block any attempt to withdraw the stopper from the syringe.

To effect easy introduction of backstop 10 over flange 22, it will be noted (referring to FIG. 9) that the height of ridge 38 may be formed such that a transitional area 38b is provided, at either end of aperture 36 in the vicinity adjacent top transitional edges 47. Thus, the height "H" (see FIG. 7) of ridge 38 may extend from virtually zero at the transitional edges 47, increasing to a position of maximal, constant height 38a directly opposite openings 40, 42. As graphically illustrated in FIG. 9a, the transition of the ridge height to a position of maximal height 38a might entail forming the position of maximal height for an arcuate section around the ridge. Alternately, as seen in FIG. 9b, the position of maximal height 38 might entail a peak portion located at the intersection of the transitional areas 38b. By providing a gradual transition of height "H" of the ridge from about zero adjacent the opening to a maximum height opposite the opening, the ridge 38 easily slides over the flange surface, so that backstop 10 can be readily guided for insertion over the flange 22. Alternatively, the progression may assume other shapes such as peaked triangular (wherein transitional area 38b is linear to constant height 38a), various sinusoidal cross-sections, or like variations as can be envisioned by the skilled artisan. Likewise, ridge 38 may assume alternate configurations such as discontinuous raised dots or protrusions which gradually peak in height to a maximum value 38a. Thus, when maximal portion 38a of ridge 38 contacts the open proximal end 19 of the syringe, additional force by a user placing the backstop 10 over the flange causes the portion 38a to be thrust over flange 22 into contact with the interior surface of syringe barrel 14 adjacent open proximal end 19, thereby providing added retention of backstop 10 relative to the syringe 14 as previously described.

As seen in FIGS. 7, 9, 14, and 15, a rib element 52 may be formed between plates 32, 30 in the enclosure 31 of backstop 10, and adjacent the back edge of the device directly opposite openings 40, 42. While here depicted formed adjacent bottom plate 30, rib 52 can also be formed adjacent top plate 32, or formed in two parts on both of the plates 30,32. The rib 52, which may be injection molded along with the remainder of backstop 10, is preferably configured for surface contact with an edge or other portion of the flange 22 when backstop 10 is fully inserted relative to flange 22. For instance, for the modified, rounded flange 22 depicted in FIG. 12a, rib 52 can be formed for contact with straight side 50 thereof (see FIG. 15). To avoid interference between the rib and the flange and to otherwise allow some rotation for backstop 10 (for instance, where backstop 10 is inserted at an angle respective of flange 22), it is preferable that rib 52 be configured so that a slight gap exists between it and flange 22 when backstop 10 is positioned onto flange 22. By providing some stabilizing contact with the edge of the flange, rib 52 serves to lessen rotation or play of backstop 10 relative to syringe 14.

Thus, the backstop 10 in accordance with the present invention is readily flexible, permitting its assembly with a syringe 14 either in the presence or absence of the syringe plunger 16, depending upon the filling and/or assembly line chosen by the manufacturer. For instance, referring to FIG. 16, as depicted in sub-FIGS. 16a–d, the stopper 20 and then syringe plunger 16 is inserted relative to the syringe barrel 14 during the assembly process (FIGS. 16a and b). Thereafter, the backstop 10 is inserted relative to the flange 22 (16c and d), representative of assembly either during the filling or sterilization processes, or affixation by an end user to a previously filled and sterilized syringe shipped by the manufacturer. By contrast, in FIG. 17, the backstop 10 is fitted shortly after stopper 20 is inserted into the syringe barrel 14 (see FIGS. 17a and b), with the plunger rod 16 thereafter mated between stopper 20 when backstop 10 is already in place on the device (see FIGS. 17c and d).

Figure 12A:
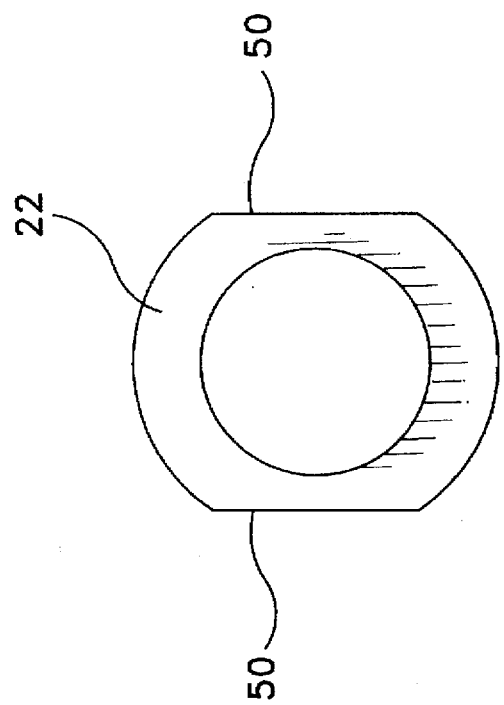
Figure 18A:
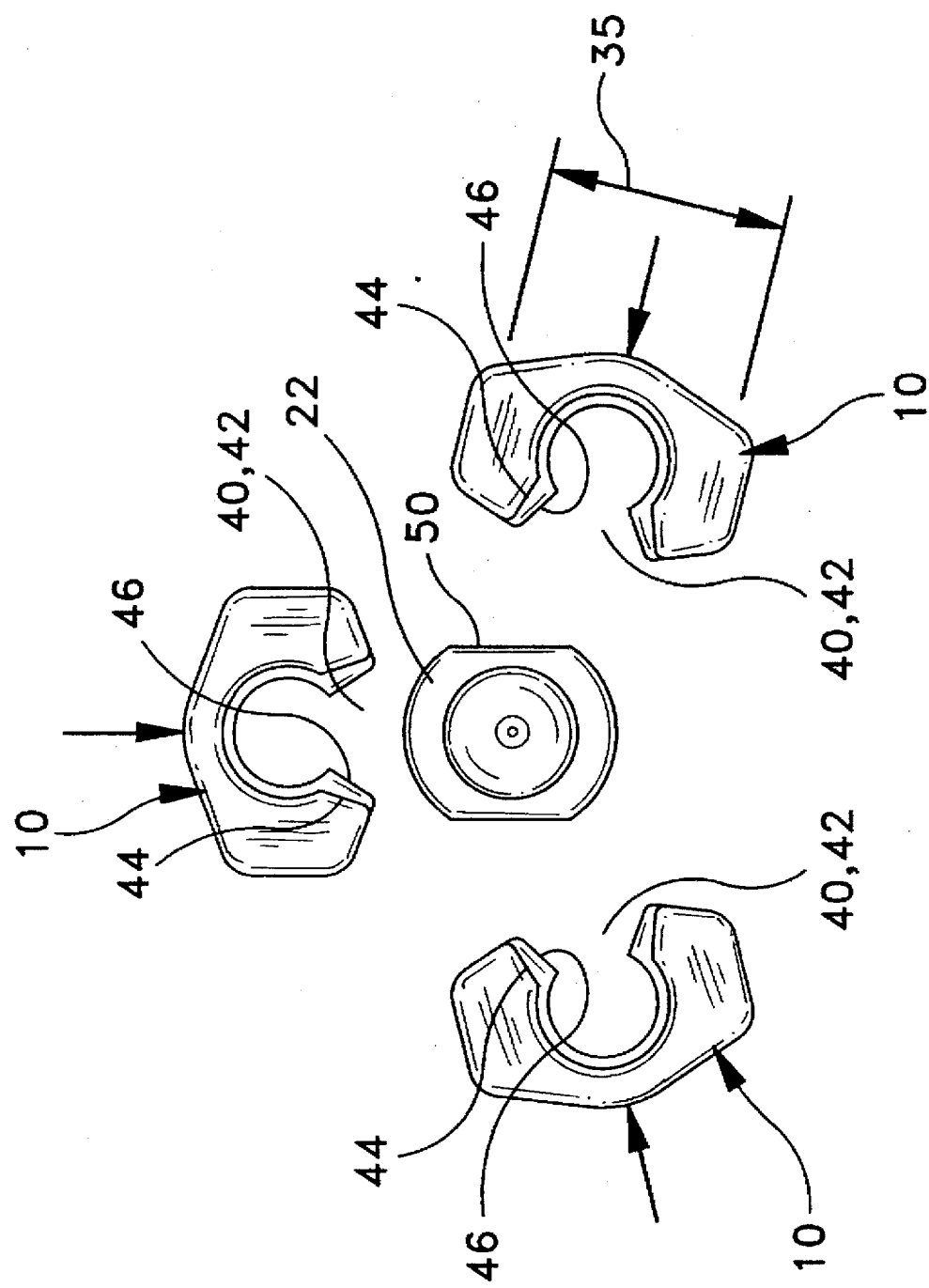
FIG. 18 depicts placement of the backstop relative to the flange at differing angles of orientation therebetween.
Figure 18B:
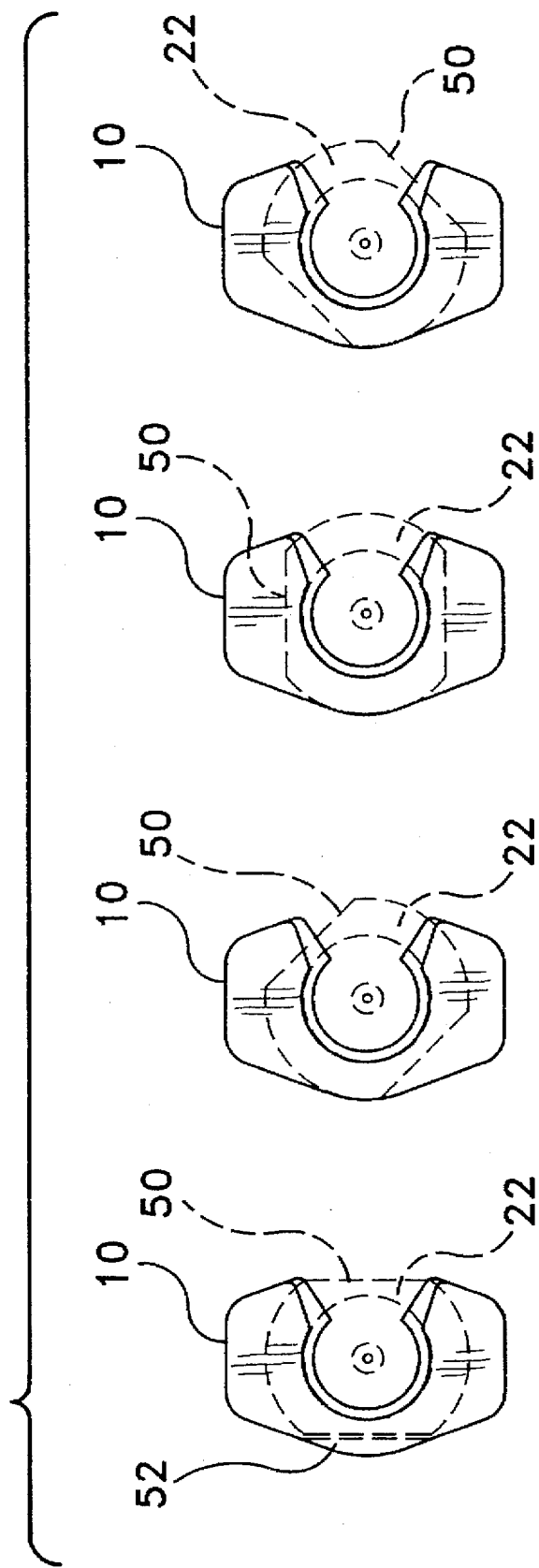

As previously noted, frontal opening 35 provides access to enclosure 31. Frontal opening 35 is configured to permit the placement of backstop 10 to flange 22, irrespective of the angular orientation between the backstop 10 and the flange 22. Referring to FIG. 18, backstop 10 is illustrated in numerous positions of angular orientation as it approaches flange 22 (see sub-FIG. 18a). Likewise, in sub-FIG. 18b, the backstop 10 is illustrated as fitted to flange 22, showing that it can be placed over the flange 22 regardless of angular orientation. For a flange 22 of modified, rounded configuration as illustrated in FIG. 12a, backstop 10 can be rotated respective of flange 22, for instance, until rib 52 makes contact with straight side 50 (see the first illustration of FIG. 18b). By providing such structure, backstop 10 is readily manipulable by a user onto flange 22, contributing to ease of use and placement.

While the embodiment principally depicted in FIGS. 1–15 is shown with both top plate 32 and bottom plate 30, it will be realized and understood by the skilled artisan that, if desired, bottom plate 30 can be eliminated in favor of a top plate extension 30a (see FIGS. 19–20) extending about all or a portion of the periphery of the device. The top plate extension 30a, together with side walls 33, define with the top plate an enclosure portion 31a which locks about the flange 22, absent contact with the walls of syringe 14 as in the prior described embodiment. While the extension 30a is depicted as jutting beneath the bottom surface of flange 22, the skilled artisan will appreciate that extension 30a could be configured for contact solely with or about the peripheral edge of flange 22 to achieve locking as described above.

It will be appreciated and understood by those skilled in the art that further and additional forms of the invention may be devised without departing from the spirit and scope of the appended claims, the invention not being limited to the specific embodiments shown.

We claim:

1. A device for preventing inadvertent removal of a stopper from a syringe, said syringe including a barrel having an open proximal end, and a flange provided adjacent said open proximal end, said barrel configured to receive a plunger rod through said open proximal end, comprising:

a backstop attachable to the flange, the backstop comprising a top plate and a bottom plate parallel to said top plate, the plates oriented to capture the flange therebetween;

said bottom plate defining an aperture therethrough adapted to engage the outside surface of said syringe barrel, said top plate defining an aperture therethrough in communication with the open proximal end of the syringe barrel;

a ridge on said top plate adjacent the top plate aperture, said ridge adapted to engage a portion of the syringe barrel adjacent the open proximal end, said ridge dimensioned to prevent withdrawal of the stopper from the syringe barrel;

a lead opening formed in each of said top and bottom plates so that said backstop is attachable to the flange irrespective of the presence or absence of a plunger rod in said barrel, each of said lead openings connected to a respective aperture formed in the plates, said lead openings oriented to permit insertion of the flange between said plates.

2. The device of claim 1, wherein at least one of said top plate or bottom plate is concave.

3. The device of claim 1, wherein at least one of said top plate or bottom plate is flat.

4. The device of claim 1, wherein said backstop is attached to said flange at a user-selected angular orientation between said lead openings and said flange, said lead openings formed in each of said top and bottom plates to permit attachment of said backstop to said flange irrespective of the angular orientation between said lead openings and said flange.

5. The device of claim 1, further comprising a rib formed adjacent an edge portion of said top or bottom plates, said rib oriented for contact with said syringe flange to reduce unwanted rotation of said backstop relative to said syringe.

6. The device of claim 1, wherein said ridge comprises a protrusion formed about a portion of the periphery of said top disk aperture, said protrusion engageable with the open proximal end of the syringe.

7. The device of claim 6, wherein the protrusion is engageable with an interior portion of the syringe barrel adjacent the open distal end.

8. The device of claim 6, wherein the protrusion is engageable with the syringe barrel adjacent the intersection of the flange and the open proximal end.

9. The device of claim 1, wherein said ridge is continuous.

10. The device of claim 1, wherein said ridge comprises one or more discontinuous portions.

11. The device of claim 1, wherein said ridge includes a height, the height of said ridge formed progressively higher as said ridge progresses away from the lead opening of said top plate.

12. The device of claim 11, wherein the height of said ridge includes a position of maximal height opposite said lead opening.

13. The device of claim 12, wherein said position of maximal height extends for an arcuate distance about said ridge.

14. The device of claim 1, wherein said top plate aperture defines a substantially frusto-conically shaped lead wall oriented towards the open proximal end of the syringe barrel, the ridge disposed at a bottom portion of said lead wall.

15. A device for preventing inadvertent withdrawal of a stopper from a syringe, said syringe including a barrel having an open proximal end and a flange adjacent said open proximal end, comprising:

a backstop attachable to the flange, the backstop comprising a top plate and a bottom plate, the plates oriented to capture the flange therebetween;

said bottom plate defining an aperture therethrough adapted to engage the outside surface of said syringe barrel, said top plate defining an aperture therethrough in communication with the open proximal end of the syringe barrel, said top plate aperture defining a substantially frusto-conical lead wall advancing from an outside surface of said top plate towards a bottom surface of said top plate;

a lead opening formed in each of said top and bottom plates, each of said lead openings including opposed transition edges connected to the respective aperture formed in the plates, said lead opening oriented to permit insertion of the flange between said plates;

a ridge disposed about the substantial periphery of said top plate lead wall, said ridge adapted to engage a portion of the syringe barrel adjacent the open proximal end, said ridge dimensioned to prevent withdrawal of the stopper from the syringe barrel.

16. The device of claim 15, wherein said ridge includes a height, the height of said ridge increasing as said ridge progresses away from the lead opening of said top plate.

17. The device of claim 16, wherein said ridge includes, in an area opposite said top plate opening, a portion of substantially equal height, wherein the height of said ridge increases towards said portion of substantially equal height as said ridge progresses away from the lead opening.

18. The device of claim 15, further comprising a rib formed adjacent an edge portion of said top or bottom plates, said rib oriented for contact with said syringe flange to reduce unwanted rotation of said backstop relative to said syringe.

19. The device of claim 15, wherein said ridge comprises an extension of an innermost edge of said top plate lead wall.

20. A device for preventing inadvertent removal of a stopper from a syringe, said syringe including a barrel having an open proximal end and a flange adjacent said open proximal end, comprising:

a backstop attachable to the flange, the backstop comprising a top plate disposed above the flange and a top plate extension oriented beneath the flange, the plate and extension oriented to capture the flange therebetween;

said top plate defining an aperture therethrough in communication with the open proximal end of the syringe barrel;

a ridge on said top plate adjacent the top plate aperture, said ridge adapted to engage a portion of the syringe barrel adjacent the open proximal end, said ridge dimensioned to prevent withdrawal of the stopper from the syringe barrel;

a lead opening formed in said top plate, said lead opening connected to the aperture formed in the plate, said lead opening oriented to permit insertion of the flange between the plates and the extension.

* * * * *